US006994867B1

(12) United States Patent
Hossainy et al.

(10) Patent No.: US 6,994,867 B1
(45) Date of Patent: *Feb. 7, 2006

(54) BIOCOMPATIBLE CARRIER CONTAINING L-ARGININE

(75) Inventors: Syed F A Hossainy, Fremont, CA (US); Eugene T Michal, San Francisco, CA (US); Charles D. Claude, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 417 days.

This patent is subject to a terminal disclaimer.

(21) Appl. No.: 10/176,499

(22) Filed: Jun. 21, 2002

(51) Int. Cl.
*A61F 2/02* (2006.01)
*A61K 9/16* (2006.01)

(52) U.S. Cl. ............. 424/423; 424/484; 424/486
(58) Field of Classification Search ......... 424/423, 424/484, 486
See application file for complete search history.

(56) References Cited

U.S. PATENT DOCUMENTS

| 2,072,303 | A | 3/1937 | Herrmann et al. ....... 128/335.5 |
| 2,386,454 | A | 10/1945 | Frosch et al. .............. 260/78 |
| 3,773,737 | A | 11/1973 | Goodman et al. ........... 260/78 |
| 3,835,175 | A | 9/1974 | Carpino et al. ............ 260/463 |
| 3,849,514 | A | 11/1974 | Gray, Jr. et al. ........... 260/857 |
| 4,226,243 | A | 10/1980 | Shalaby et al. .......... 128/335.5 |
| 4,329,383 | A | 5/1982 | Joh ............................ 428/36 |
| 4,343,931 | A | 8/1982 | Barrows ..................... 528/291 |
| 4,529,792 | A | 7/1985 | Barrows ..................... 528/291 |
| 4,611,051 | A | 9/1986 | Hayes et al. ............. 528/295.3 |
| 4,656,242 | A | 4/1987 | Swan et al. .............. 528/295.3 |
| 4,733,665 | A | 3/1988 | Palmaz ...................... 128/343 |
| 4,800,882 | A | 1/1989 | Gianturco ................... 128/343 |
| 4,882,168 | A | 11/1989 | Casey et al. ................ 424/468 |
| 4,886,062 | A | 12/1989 | Wiktor ....................... 128/343 |
| 4,908,404 | A | 3/1990 | Benedict et al. ......... 525/54.11 |
| 4,917,309 | A | 4/1990 | Zander et al. ................. 241/5 |
| 4,931,287 | A | 6/1990 | Bae et al. .................... 424/484 |
| 4,941,870 | A | 7/1990 | Okada et al. ................. 600/36 |
| 4,977,901 | A | 12/1990 | Ofstead ...................... 128/772 |
| 5,019,096 | A | 5/1991 | Fox, Jr. et al. ................ 623/1 |
| 5,025,001 | A | 6/1991 | Loscalzo et al. ............. 514/91 |
| 5,100,992 | A | 3/1992 | Cohn et al. ................. 424/501 |
| 5,112,457 | A | 5/1992 | Marchant ................... 204/165 |
| 5,133,742 | A | 7/1992 | Pinchuk ....................... 623/1 |
| 5,155,137 | A | 10/1992 | Keefer et al. ............... 514/611 |
| 5,163,952 | A | 11/1992 | Froix .......................... 623/1 |
| 5,165,919 | A | 11/1992 | Sasaki et al. ............... 424/488 |
| 5,187,183 | A | 2/1993 | Loscalzo et al. ............ 514/400 |
| 5,202,129 | A | 4/1993 | Samejima et al. .......... 424/489 |
| 5,219,980 | A | 6/1993 | Swidler ...................... 528/272 |
| 5,258,020 | A | 11/1993 | Froix .......................... 623/1 |

(Continued)

FOREIGN PATENT DOCUMENTS

DE 42 24 401 1/1994

(Continued)

OTHER PUBLICATIONS

Anderson et al., *Nitric-Oxide and Nitrovasodilators: Similarities, Differences and Potential Interactions*, JACC 24(2): 555-566 (1994).

(Continued)

*Primary Examiner*—Carlos A. Azpuru
(74) *Attorney, Agent, or Firm*—Squire, Sanders & Dempsey LLP

(57) ABSTRACT

L-arginine conjugated to a polymeric matrix is disclosed. The matrix can be used as, for example, a coating for an implantable medical device such as a stent.

33 Claims, 5 Drawing Sheets

U.S. PATENT DOCUMENTS

| | | | | |
|---|---|---|---|---|
| 5,272,012 | A | 12/1993 | Opolski | 428/423.1 |
| 5,292,516 | A | 3/1994 | Viegas et al. | 424/423 |
| 5,298,260 | A | 3/1994 | Viegas et al. | 424/486 |
| 5,300,295 | A | 4/1994 | Viegas et al. | 424/427 |
| 5,306,501 | A | 4/1994 | Viegas et al. | 424/423 |
| 5,306,786 | A | 4/1994 | Moens et al. | 525/437 |
| 5,328,471 | A | 7/1994 | Slepian | 604/101 |
| 5,330,768 | A | 7/1994 | Park et al. | 424/501 |
| 5,356,890 | A | 10/1994 | Loscalzo et al. | 514/210 |
| 5,366,997 | A | 11/1994 | Keefer et al. | 614/611 |
| 5,380,299 | A | 1/1995 | Fearnot et al. | 604/265 |
| 5,405,919 | A | 4/1995 | Keefer et al. | 525/377 |
| 5,417,981 | A | 5/1995 | Endo et al. | 424/486 |
| 5,424,077 | A | 6/1995 | Lajoie | 424/641 |
| 5,428,070 | A | 6/1995 | Cooke et al. | 514/557 |
| 5,447,724 | A | 9/1995 | Helmus et al. | 424/426 |
| 5,455,040 | A | 10/1995 | Marchant | 424/426 |
| 5,462,990 | A | 10/1995 | Hubbell et al. | 525/54.1 |
| 5,464,650 | A | 11/1995 | Berg et al. | 427/2.3 |
| 5,482,720 | A | 1/1996 | Murphy et al. | 424/489 |
| 5,485,496 | A | 1/1996 | Lee et al. | 378/64 |
| 5,516,881 | A | 5/1996 | Lee et al. | 528/320 |
| 5,536,723 | A | 7/1996 | Loscalzo et al. | 514/247 |
| 5,543,099 | A | 8/1996 | Zhang et al. | 264/115 |
| 5,569,463 | A | 10/1996 | Helmus et al. | 424/426 |
| 5,578,073 | A | 11/1996 | Haimovich et al. | 623/1 |
| 5,584,877 | A | 12/1996 | Miyake et al. | 623/1 |
| 5,605,696 | A | 2/1997 | Eury et al. | 424/423 |
| 5,607,467 | A | 3/1997 | Froix | 623/1 |
| 5,609,629 | A | 3/1997 | Fearnot et al. | 623/1 |
| 5,610,241 | A | 3/1997 | Lee et al. | 525/411 |
| 5,616,338 | A | 4/1997 | Fox, Jr. et al. | 424/423 |
| 5,624,411 | A | 4/1997 | Tuch | 604/265 |
| 5,628,730 | A | 5/1997 | Shapland et al. | 604/21 |
| 5,639,441 | A | 6/1997 | Sievers et al. | 424/9.3 |
| 5,644,020 | A | 7/1997 | Timmermann et al. | 528/288 |
| 5,649,977 | A | 7/1997 | Campbell | 623/1 |
| 5,650,442 | A | 7/1997 | Mitchell et al. | 514/611 |
| 5,658,995 | A | 8/1997 | Kohn et al. | 525/432 |
| 5,667,767 | A | 9/1997 | Greff et al. | 424/9.411 |
| 5,670,558 | A | 9/1997 | Onishi et al. | 523/112 |
| 5,674,242 | A | 10/1997 | Phan et al. | 606/198 |
| 5,679,400 | A | 10/1997 | Tuch | 427/2.14 |
| 5,700,286 | A | 12/1997 | Tartaglia et al. | 623/1 |
| 5,702,754 | A | 12/1997 | Zhong | 427/2.12 |
| 5,711,958 | A | 1/1998 | Cohn et al. | 424/423 |
| 5,716,981 | A | 2/1998 | Hunter et al. | 514/449 |
| 5,721,131 | A | 2/1998 | Rudolph et al. | 435/240 |
| 5,723,219 | A | 3/1998 | Kolluri et al. | 428/411.1 |
| 5,735,897 | A | 4/1998 | Buirge | 623/12 |
| 5,746,998 | A | 5/1998 | Torchilin et al. | 424/9.4 |
| 5,759,205 | A | 6/1998 | Valentini | 623/16 |
| 5,776,184 | A | 7/1998 | Tuch | 623/1 |
| 5,783,657 | A | 7/1998 | Pavlin et al. | 528/310 |
| 5,788,979 | A | 8/1998 | Alt et al. | 424/426 |
| 5,800,392 | A | 9/1998 | Racchini | 604/96 |
| 5,804,318 | A | 9/1998 | Pinchuk et al. | 428/421 |
| 5,820,917 | A | 10/1998 | Tuch | 427/2.1 |
| 5,824,048 | A | 10/1998 | Tuch | 623/1 |
| 5,824,049 | A | 10/1998 | Ragheb et al. | 623/1 |
| 5,830,178 | A | 11/1998 | Jones et al. | 604/49 |
| 5,837,008 | A | 11/1998 | Berg et al. | 623/1 |
| 5,837,313 | A | 11/1998 | Ding et al. | 427/2.21 |
| 5,849,859 | A | 12/1998 | Acemoglu | 528/271 |
| 5,851,508 | A | 12/1998 | Greff et al. | 424/9.411 |
| 5,852,058 | A | 12/1998 | Cooke et al. | 514/564 |
| 5,854,376 | A | 12/1998 | Higashi | 528/288 |
| 5,858,746 | A | 1/1999 | Hubbell et al. | 435/177 |
| 5,861,168 | A * | 1/1999 | Cooke et al. | 424/424 |
| 5,865,814 | A | 2/1999 | Tuch | 604/265 |
| 5,869,127 | A | 2/1999 | Zhong | 427/2.12 |
| 5,873,904 | A | 2/1999 | Ragheb et al. | 623/1 |
| 5,874,165 | A | 2/1999 | Drumheller | 428/308.4 |
| 5,876,433 | A | 3/1999 | Lunn | 623/1 |
| 5,877,224 | A | 3/1999 | Brocchini et al. | 514/772.2 |
| 5,879,713 | A | 3/1999 | Roth et al. | 424/489 |
| 5,891,459 | A | 4/1999 | Cooke et al. | 424/439 |
| 5,902,875 | A | 5/1999 | Roby et al. | 528/310 |
| 5,905,168 | A | 5/1999 | Dos Santos et al. | 562/590 |
| 5,910,564 | A | 6/1999 | Gruning et al. | 528/310 |
| 5,914,387 | A | 6/1999 | Roby et al. | 528/310 |
| 5,919,893 | A | 7/1999 | Roby et al. | 525/411 |
| 5,925,720 | A | 7/1999 | Kataoka et al. | 525/523 |
| 5,932,299 | A | 8/1999 | Katoot | 427/508 |
| 5,945,452 | A | 8/1999 | Cooke et al. | 514/564 |
| 5,955,509 | A | 9/1999 | Webber et al. | 514/772.7 |
| 5,958,385 | A | 9/1999 | Tondeur et al. | 424/61 |
| 5,962,138 | A | 10/1999 | Kolluri et al. | 428/411.1 |
| 5,971,954 | A | 10/1999 | Conway et al. | 604/96 |
| 5,980,928 | A | 11/1999 | Terry | 424/427 |
| 5,980,972 | A | 11/1999 | Ding | 427/2.24 |
| 5,997,517 | A | 12/1999 | Whitbourne | 604/265 |
| 6,010,530 | A | 1/2000 | Goicoechea | 623/1 |
| 6,011,125 | A | 1/2000 | Lohmeijer et al. | 525/440 |
| 6,015,541 | A | 1/2000 | Greff et al. | 424/1.25 |
| 6,033,582 | A | 3/2000 | Lee et al. | 216/37 |
| 6,034,204 | A | 3/2000 | Mohr et al. | 528/328 |
| 6,042,875 | A | 3/2000 | Ding et al. | 427/2.24 |
| 6,051,576 | A | 4/2000 | Ashton et al. | 514/255 |
| 6,051,648 | A | 4/2000 | Rhee et al. | 525/54.1 |
| 6,054,553 | A | 4/2000 | Groth et al. | 528/335 |
| 6,056,993 | A | 5/2000 | Leidner et al. | 427/2.25 |
| 6,060,451 | A | 5/2000 | DiMaio et al. | 514/13 |
| 6,060,518 | A | 5/2000 | Kabanov et al. | 514/781 |
| 6,060,534 | A | 5/2000 | Ronan et al. | 523/113 |
| 6,063,432 | A | 5/2000 | Maxwell et al. | 426/656 |
| 6,077,543 | A | 6/2000 | Gordon et al. | 424/489 |
| 6,080,488 | A | 6/2000 | Hostettler et al. | 428/423.3 |
| 6,095,134 | A | 8/2000 | Sievers et al. | 128/200.14 |
| 6,096,070 | A | 8/2000 | Ragheb et al. | 623/1 |
| 6,099,562 | A | 8/2000 | Ding et al. | 623/1.46 |
| 6,110,188 | A | 8/2000 | Narciso, Jr. | 606/153 |
| 6,110,483 | A | 8/2000 | Whitbourne et al. | 424/423 |
| 6,113,629 | A | 9/2000 | Ken | 623/1.1 |
| 6,117,872 | A | 9/2000 | Maxwell et al. | 514/249 |
| 6,120,491 | A | 9/2000 | Kohn et al. | 604/502 |
| 6,120,536 | A | 9/2000 | Ding et al. | 623/1.43 |
| 6,120,788 | A | 9/2000 | Barrows | 424/426 |
| 6,120,904 | A | 9/2000 | Hostettler et al. | 428/423.3 |
| 6,121,027 | A | 9/2000 | Clapper et al. | 435/180 |
| 6,129,761 | A | 10/2000 | Hubbell | 623/11 |
| 6,136,333 | A | 10/2000 | Cohn et al. | 424/423 |
| 6,143,354 | A | 11/2000 | Koulik et al. | 427/2.24 |
| 6,153,252 | A | 11/2000 | Hossainy et al. | 427/2.3 |
| 6,159,978 | A | 12/2000 | Myers et al. | 514/252.1 |
| 6,165,212 | A | 12/2000 | Dereume et al. | 623/1.13 |
| 6,172,167 | B1 | 1/2001 | Stapert et al. | 525/420 |
| 6,177,523 | B1 | 1/2001 | Reich et al. | 525/459 |
| 6,180,632 | B1 | 1/2001 | Myers et al. | 514/252.1 |
| 6,183,783 | B1 | 2/2001 | Benoit et al. | 424/497 |
| 6,203,551 | B1 | 3/2001 | Wu | 606/108 |
| 6,211,249 | B1 | 4/2001 | Cohn et al. | 514/772.1 |
| 6,214,901 | B1 | 4/2001 | Chudzik et al. | 523/113 |
| 6,228,346 | B1 | 5/2001 | Zhang et al. | 424/45 |
| 6,231,600 | B1 | 5/2001 | Zhong | 623/1.42 |
| 6,240,616 | B1 | 6/2001 | Yan | 29/527.2 |
| 6,245,753 | B1 | 6/2001 | Byun et al. | 514/56 |
| 6,245,760 | B1 | 6/2001 | He et al. | 514/234.8 |
| 6,248,129 | B1 | 6/2001 | Froix | 623/1.42 |
| 6,251,136 | B1 | 6/2001 | Guruwaiya et al. | 623/1.46 |
| 6,254,632 | B1 | 7/2001 | Wu et al. | 623/1.15 |
| 6,258,121 | B1 | 7/2001 | Yang et al. | 623/1.46 |
| 6,258,371 | B1 | 7/2001 | Koulik et al. | 424/422 |
| 6,262,034 | B1 | 7/2001 | Mathiowitz et al. | 514/44 |

| Patent | Date | Inventor | Class |
|---|---|---|---|
| 6,270,788 B1 | 8/2001 | Koulik et al. | 424/423 |
| 6,277,449 B1 | 8/2001 | Kolluri et al. | 427/289 |
| 6,283,947 B1 | 9/2001 | Mirzaee | 604/264 |
| 6,283,949 B1 | 9/2001 | Roorda | 604/288.02 |
| 6,284,305 B1 | 9/2001 | Ding et al. | 427/2.28 |
| 6,287,628 B1 | 9/2001 | Hossainy et al. | 427/2.3 |
| 6,299,604 B1 | 10/2001 | Ragheb et al. | 604/265 |
| 6,306,166 B1 | 10/2001 | Barry et al. | 623/1.46 |
| 6,306,176 B1 | 10/2001 | Whitbourne | 623/23.59 |
| 6,306,993 B1 | 10/2001 | Rothbard et al. | 526/304 |
| 6,331,313 B1 | 12/2001 | Wong et al. | 424/427 |
| 6,335,029 B1 | 1/2002 | Kamath et al. | 424/423 |
| 6,344,035 B1 | 2/2002 | Chudzik et al. | 604/265 |
| 6,346,110 B2 | 2/2002 | Wu | 606/108 |
| 6,358,556 B1 | 3/2002 | Ding et al. | 427/2.24 |
| 6,379,381 B1 | 4/2002 | Hossainy et al. | 623/1.42 |
| 6,387,379 B1 | 5/2002 | Goldberg et al. | 424/400 |
| 6,395,326 B1 | 5/2002 | Castro et al. | 427/2.24 |
| 6,419,692 B1 | 7/2002 | Yang et al. | 623/1.15 |
| 6,451,373 B1 | 9/2002 | Hossainy et al. | 427/2.25 |
| 6,482,834 B2 | 11/2002 | Spada et al. | 514/311 |
| 6,494,862 B1 | 12/2002 | Ray et al. | 604/96.01 |
| 6,503,538 B1 | 1/2003 | Chu et al. | 424/497 |
| 6,503,556 B2 | 1/2003 | Harish et al. | 427/2.24 |
| 6,503,954 B1 | 1/2003 | Bhat et al. | 514/772.2 |
| 6,506,437 B1 | 1/2003 | Harish et al. | 427/2.25 |
| 6,524,347 B1 | 2/2003 | Myers et al. | 514/252.1 |
| 6,527,801 B1 | 3/2003 | Dutta | 623/1.46 |
| 6,527,863 B1 | 3/2003 | Pacetti et al. | 118/500 |
| 6,528,526 B1 | 3/2003 | Myers et al. | 214/311 |
| 6,530,950 B1 | 3/2003 | Alvarado et al. | 623/1.13 |
| 6,530,951 B1 | 3/2003 | Bates et al. | 623/1.45 |
| 6,540,776 B2 | 4/2003 | Sanders Millare et al. | 623/1.15 |
| 6,544,223 B1 | 4/2003 | Kokish | 604/103.01 |
| 6,544,543 B1 | 4/2003 | Mandrusov et al. | 424/422 |
| 6,544,582 B1 | 4/2003 | Yoe | 427/2.24 |
| 6,555,157 B1 | 4/2003 | Hossainy | 427/2.24 |
| 6,558,733 B1 | 5/2003 | Hossainy et al. | 427/2.24 |
| 6,565,659 B1 | 5/2003 | Pacetti et al. | 118/500 |
| 6,572,644 B1 | 6/2003 | Moein | 623/1.11 |
| 6,585,755 B2 | 7/2003 | Jackson et al. | 623/1.15 |
| 6,585,765 B1 | 7/2003 | Hossainy et al. | 623/1.45 |
| 6,585,926 B1 | 7/2003 | Mirzaee | 264/400 |
| 6,605,154 B1 | 8/2003 | Villareal | 118/500 |
| 6,616,765 B1 | 9/2003 | Hossaony et al. | 623/1.45 |
| 6,623,448 B2 | 9/2003 | Slater | 604/95.01 |
| 6,625,486 B2 | 9/2003 | Lundkvist et al. | 604/21 |
| 6,645,135 B1 | 11/2003 | Bhat | 600/3 |
| 6,645,195 B1 | 11/2003 | Bhat et al. | 604/528 |
| 6,656,216 B1 | 12/2003 | Hossainy et al. | 623/1.13 |
| 6,656,506 B1 | 12/2003 | Wu et al. | 424/489 |
| 6,660,034 B1 | 12/2003 | Mandrusov et al. | 623/1.42 |
| 6,663,662 B2 | 12/2003 | Pacetti et al. | 623/1.13 |
| 6,663,880 B1 | 12/2003 | Roorda et al. | 424/423 |
| 6,666,880 B1 | 12/2003 | Chiu et al. | 623/1.11 |
| 6,673,154 B1 | 1/2004 | Pacetti et al. | 118/500 |
| 6,673,385 B1 | 1/2004 | Ding et al. | 427/2.28 |
| 6,689,099 B2 | 2/2004 | Mirzaee | 604/107 |
| 6,695,920 B1 | 2/2004 | Pacetti et al. | 118/500 |
| 6,706,013 B1 | 3/2004 | Bhat et al. | 604/96.01 |
| 6,709,514 B1 | 3/2004 | Hossainy | 118/52 |
| 6,712,845 B2 | 3/2004 | Hossainy | 623/1.42 |
| 6,713,119 B2 | 3/2004 | Hossainy et al. | 427/2.25 |
| 6,716,444 B1 | 4/2004 | Castro et al. | 424/422 |
| 6,723,120 B2 | 4/2004 | Yan | 623/1.15 |
| 6,733,768 B2 | 5/2004 | Hossainy et al. | 424/426 |
| 6,740,040 B1 | 5/2004 | Mandrusov et al. | 600/439 |
| 6,743,462 B1 | 6/2004 | Pacetti | 427/2.24 |
| 6,746,481 B1 | 6/2004 | Larik et al. | |
| 6,749,626 B1 | 6/2004 | Bhat et al. | 623/1.1 |
| 6,753,071 B1 | 6/2004 | Pacetti et al. | 428/212 |
| 6,758,859 B1 | 7/2004 | Dang et al. | 623/1.15 |
| 6,759,054 B2 | 7/2004 | Chen et al. | 424/423 |
| 6,764,505 B1 | 7/2004 | Hossainy et al. | 623/1.15 |
| 2001/0007083 A1 | 7/2001 | Roorda | 623/1.15 |
| 2001/0014717 A1 | 8/2001 | Hossainy et al. | 525/60 |
| 2001/0018469 A1 | 8/2001 | Chen et al. | 523/121 |
| 2001/0020011 A1 | 9/2001 | Mathiowitz et al. | 514/44 |
| 2001/0029351 A1 | 10/2001 | Falotico et al. | 604/103.02 |
| 2001/0037145 A1 | 11/2001 | Guruwaiya et al. | 623/1.15 |
| 2001/0051608 A1 | 12/2001 | Mathiowitz et al. | 514/44 |
| 2002/0005206 A1 | 1/2002 | Falotico et al. | 128/898 |
| 2002/0007213 A1 | 1/2002 | Falotico et al. | 623/1.21 |
| 2002/0007214 A1 | 1/2002 | Falotico | 623/1.21 |
| 2002/0007215 A1 | 1/2002 | Falotico et al. | 623/1.21 |
| 2002/0009604 A1 | 1/2002 | Zamora et al. | 428/450 |
| 2002/0016625 A1 | 2/2002 | Falotico et al. | 623/1.13 |
| 2002/0032414 A1 | 3/2002 | Ragheb et al. | 604/265 |
| 2002/0032434 A1 | 3/2002 | Chudzik et al. | 604/890.1 |
| 2002/0051730 A1 | 5/2002 | Bodnar et al. | 422/33 |
| 2002/0071822 A1 | 6/2002 | Uhrich | 424/78.37 |
| 2002/0077693 A1 | 6/2002 | Barclay et al. | 623/1.13 |
| 2002/0082679 A1 | 6/2002 | Sirhan et al. | 623/1.15 |
| 2002/0087123 A1 | 7/2002 | Hossainy et al. | 604/198 |
| 2002/0091433 A1 | 7/2002 | Ding et al. | 623/1.2 |
| 2002/0094440 A1 | 7/2002 | Llanos et al. | 428/421 |
| 2002/0111590 A1 | 8/2002 | Davila et al. | 604/265 |
| 2002/0120326 A1 | 8/2002 | Michal | 623/1.15 |
| 2002/0123801 A1 | 9/2002 | Pacetti et al. | 623/1.46 |
| 2002/0142039 A1 | 10/2002 | Claude | 424/486 |
| 2002/0155212 A1 | 10/2002 | Hossainy | 427/2.25 |
| 2002/0165608 A1 | 11/2002 | Llanos et al. | 623/1.45 |
| 2002/0176849 A1 | 11/2002 | Slepian | 424/93.7 |
| 2002/0183581 A1 | 12/2002 | Yoe et al. | 600/3 |
| 2002/0188037 A1 | 12/2002 | Chudzik et al. | 523/112 |
| 2002/0188277 A1 | 12/2002 | Roorda et al. | 604/523 |
| 2003/0004141 A1 | 1/2003 | Brown | 514/152 |
| 2003/0028243 A1 | 2/2003 | Bates et al. | 623/1.15 |
| 2003/0028244 A1 | 2/2003 | Bates et al. | 623/1.15 |
| 2003/0031780 A1 | 2/2003 | Chudzik et al. | 427/2.1 |
| 2003/0032767 A1 | 2/2003 | Tada et al. | 528/310 |
| 2003/0036794 A1 | 2/2003 | Ragheb et al. | 623/1.15 |
| 2003/0039689 A1 | 2/2003 | Chen et al. | 424/468 |
| 2003/0040712 A1 | 2/2003 | Ray et al. | 604/173 |
| 2003/0040790 A1 | 2/2003 | Furst | 623/1.11 |
| 2003/0059520 A1 | 3/2003 | Chen et al. | 427/2.1 |
| 2003/0060877 A1 | 3/2003 | Falotico et al. | 623/1.42 |
| 2003/0065377 A1 | 4/2003 | Davila et al. | 623/1.13 |
| 2003/0072868 A1 | 4/2003 | Harish et al. | 427/2.24 |
| 2003/0073961 A1 | 4/2003 | Happ | 604/274 |
| 2003/0083646 A1 | 5/2003 | Sirhan et al. | 604/891.1 |
| 2003/0083739 A1 | 5/2003 | Cafferata | 623/1.42 |
| 2003/0097088 A1 | 5/2003 | Pacetti | 604/19 |
| 2003/0097173 A1 | 5/2003 | Dutta | 623/1.38 |
| 2003/0099712 A1 | 5/2003 | Jayaraman | 424/486 |
| 2003/0105518 A1 | 6/2003 | Dutta | 623/1.38 |
| 2003/0113439 A1 | 6/2003 | Pacetti et al. | 427/2.24 |
| 2003/0150380 A1 | 8/2003 | Yoe | 118/423 |
| 2003/0157241 A1 | 8/2003 | Hossainy et al. | 427/2.24 |
| 2003/0158517 A1 | 8/2003 | Kokish | 604/103.01 |
| 2003/0190406 A1 | 10/2003 | Hossainy et al. | 427/2.25 |
| 2003/0207020 A1 | 11/2003 | Villareal | 427/2.24 |
| 2003/0211230 A1 | 11/2003 | Pacetti et al. | 427/2.24 |
| 2004/0018296 A1 | 1/2004 | Castro et al. | 427/2.25 |
| 2004/0029952 A1 | 2/2004 | Chen et al. | 514/449 |
| 2004/0047978 A1 | 3/2004 | Hossainy et al. | 427/2.1 |
| 2004/0047980 A1 | 3/2004 | Pacetti et al. | 427/2.25 |
| 2004/0052858 A1 | 3/2004 | Wu et al. | 424/490 |
| 2004/0052859 A1 | 3/2004 | Wu et al. | 424/490 |
| 2004/0054104 A1 | 3/2004 | Pacetti | 526/242 |
| 2004/0060508 A1 | 4/2004 | Pacetti et al. | 118/264 |
| 2004/0062853 A1 | 4/2004 | Pacetti et al. | 427/2.1 |
| 2004/0063805 A1 | 4/2004 | Pacetti et al. | 523/113 |
| 2004/0071861 A1 | 4/2004 | Mandrusov et al. | 427/2.24 |
| 2004/0072922 A1 | 4/2004 | Hossainy et al. | 523/113 |
| 2004/0073298 A1 | 4/2004 | Hossainy | 623/1.46 |

| | | | | | | |
|---|---|---|---|---|---|---|
| 2004/0086542 | A1 | 5/2004 | Hossainy et al. ........... 424/423 | WO | WO 01/74414 | 10/2001 |
| 2004/0086550 | A1 | 5/2004 | Roorda et al. .............. 424/448 | WO | WO 02/03890 | 1/2002 |
| 2004/0096504 | A1 | 5/2004 | Michal ....................... 424/471 | WO | WO 02/26162 | 4/2002 |
| 2004/0098117 | A1 | 5/2004 | Hossainy et al. .......... 623/1.42 | WO | WO 02/34311 | 5/2002 |

FOREIGN PATENT DOCUMENTS

| | | |
|---|---|---|
| EP | 0 301 856 | 2/1989 |
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 677 332 A2 | 10/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 94/28721 | 12/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 97/16983 | 5/1997 |
| WO | WO 97/45105 | 12/1997 |
| WO | WO 97/46590 | 12/1997 |
| WO | WO 98/06389 | 2/1998 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 98/49199 | 11/1998 |
| WO | WO 99/00070 | 1/1999 |
| WO | WO 99/01118 | 1/1999 |
| WO | WO 99/38546 | 8/1999 |
| WO | WO 99/59433 | 11/1999 |
| WO | WO 99/63981 | 12/1999 |
| WO | WO 99/66921 | 12/1999 |
| WO | WO 00/02599 | 1/2000 |
| WO | WO 00/12147 | 3/2000 |
| WO | WO 00/18446 | 4/2000 |
| WO | WO 00/46395 | 8/2000 |
| WO | WO 00/64506 | 11/2000 |
| WO | WO 00/74701 | 12/2000 |
| WO | WO 01/01890 A1 | 1/2001 |
| WO | WO 01/08684 | 2/2001 |
| WO | WO 01/13957 | 3/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/62297 | 8/2001 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 04/000383 | 12/2003 |
| WO | WO 04/009145 | 1/2004 |

OTHER PUBLICATIONS

Anderson et al., *Close Relation of Endothelial Function in the Human Coronary and Peripheral Circulations*, JACC 26(5):1235-1241 (1995).

Bode-Boger et al., *Elevated L-Arginine/Dimethylarginine Ratio Contributes to Enhanced Systemic NO Production by Dietary L-Arginine in Hypercholesterolemic Rabbits*, Biochem. And Biophys. Res. Comm. 219:598-603 (1996).

Bodmer et al., *Enhanced Recognition of a Modified Peptide Antigen by Cytotoxic T Cells Specific for Influenza Nucleoprotein*, Cell 52:253-258 (1988).

Boger et al., *An Endogenous Inhibitor of Nitric Oxide Synthase Regulates Endothelial Adhesiveness for Monocytes*, JACC 36(7):2287-2295 (2000).

Boger et al., *Asymmetric Dimethylarginine (ADMA):A Novel Risk Factor for Endothelial Dysfunction: Its Role in Hypercholesterolemia*, Circ. 98:1842-1847 (1998).

Boger et al., *Asymmetric Dimethylarginine: A Novel Risk Factor for Endothelial Dysfunction*, Circ. 96(8):I-32 (1997).

Boger et al., *The Endogenous NO Synthase Inhibitor Asymmetric Dimethyl-L-Arginine (ADMA) Regulates Endothelial NO Production and Adhesiveness for Monocytes* (Abstract J5), Nitric Oxide 2:126 (1998).

Boger et al., *Restoring Vascular Nitric Oxide Formation by L-Arginine Improves the Symptoms of Intermittent Claudication in Patients With Peripheral Arterial Occlusive Disease*, J. Am. Coll. Cardiol. 32:1336-1344 (1998).

Candipan et al., *Dietary L-Arginine Attenuates Macrophage Infiltration and Intimal Hyperplasia After Balloon Injury* (Abstract 765-2), JACC 25:275A (1995).

Candipan et al., *Regression or Progression: Dependency on Vascular Nitric Oxide*, Arterioscler. Thromb. Vasc. Biol. 16(1):44-50 (1996).

Chan et al., *Asymmetric Dimethylarginine Increases Mononuclear Cell Adhesiveness in Hypercholesterolemic Humans*, Arterioscler. Thromb. Vasc. Biol. 20:1040-1046 (2002).

Cooke et al., *Arginine: A New Therapy for Atherosclerosis?* Circ. 95(2):311-312 (1997).

Cooke et al., *Cytoprotective Effects of Nitric Oxide*, Circ. 88(5)1:2451-2454 (1993).

Cooke et al., *Derangements of the Nitric Oxide Synthase Pathway, L-Arginine, and Cardiovascular Diseases*, Circ. 96(2):379-382 (1997).

Cooke et al., *Diffuse Coronary Artery Disease and Endothelial Dysfunction: Form Follows Function*, ACC Curr. J. Rev. pp. 19-25 (Nov./Dec. 2000).

Cooke et al., *Regression and Progression: Dependency Upon NO* (Abstract), J. Investi. Med. 43(2) Suppl. 2:211A (1995).

Cooke et al., *The Role of Endothelium-Derived Nitric Oxide in Atherosclerosis,* Adv. Vasc. Path. 1150:3-14 (1997).

Cooke, *Does ADMA Cause Endothelial Dysfunction?,* Arterioscler. Thromb. Vasc. Biol. 20:2032-2037 (2002).

Cooke, *Enhancement of Endogenous Vascular Nitric Oxide: A New Therapeutic Strategy for Restenosis* (Abstract 301), Eur. J. Clin. Investi. 28:A53 (1998).

Cooke, *Is Atherosclerosis an Arginine Deficiency Disease?,* J. Investi. Med. 46(8):377-380 (1998).

Cooke, *Nutriceuticals for Cardiovascular Health,* Am. J. Cardio., 82(10A):43S-46S (1998).

Cooke, *Role of Nitric Oxide in Progression and Regression of Atherosclerosis,* West. J. Med. 164(5):419-424 (1996).

Cooke, *The 1998 Nobel Prize in Medicine: Clinical Implications for 1999 and Beyond,* Vasc. Med. 4:57-60 (1999).

Cooke, *The Endothelium: A New Target for Therapy,* Vasc. Med. 5:49-43 (2000).

Cooke, *The Pathophysiology Of Peripheral Arterial Disease: Rational Targets for Drug Intervention,* Vasc. Med. 2:227-230 (1997).

Creager et al., *L-Arginine Improves Endothelium-Dependent Vasodilation in Hypercholesterolemic Humans,* J. Clin. Investi. 90:1248-1253 (1992).

Drexler et al., *Effect of L-Arginine on Coronary Endothelial Function in Cardiac Transplant Recipients: Relation to Vessel Wall Morphology,* Circ. 89(4):1615-1623 (1994).

Drexler et al., *Endothelial Dysfunction in the Coronary Circulation After Cardiac Transplantation: Effect of L-Arginine* (Abstract I356), Circ. 86(4) Supp:1418 (1992).

Dulak et al., *Nitric Oxide Induces the Synthesis of Vascular Endothelial Growth Factor by Rat Vascular Smooth Muscle Cells,* Arterioscler. Thromb. Vasc. Biol. 20:659-666 (2002).

http://www.lf2.cuni.dz/physiolres/1997/issue5/iss5cl6.html,

Farghali et al., *Effects of Nitroprusside as a Nitric Oxide Donor on Anoxia/Reoxygenation and D-galactosamine Hepatic Injuries: a Study in Perfused Hepatocytes* (Summary), Physiol. Res. 46(5):363-369 (1997).

Gaiser et al., *Lethal Short-Limbed Dwarfism in Transgenic Mice with an Arginine to Cysteine Substitution in Alpha-I (II) Procollagen* (Abstract 3369), Mol. Biol. Cell 7:579A (1996).

Ganz et al., *Coronary Vasospasm in Humans—The Role of Atherosclerosis and of Impaired Endothelial Vasodilator Function,* Basic Res. Cardiol. 86(Suppl 2):215-222 (1991).

Gregory et al., *Enhanced Nitric Oxide Production Induced by the Administration of L-Arginine Does Not Inhibit Arterial Neointimal Formation After Overwhelming Alloimmune Injury,* J. Heart Lung Transplant. 15(1)Part 1:58-66 (1996).

Gregory et al., *Nitrix Oxide Induced by the Administration of L-Arginine Does Not Inhibit Arterial Neointimal Formation Following Alloimmune Injury* (Abstract 41), J. Heart Lung Transplant. 14(1)Part 2:S45 (1995).

Heeschen et al., *Hypercholesterolemia Impairs Angiogenic Response to Hind Limb Ischemia: Role of ADMA* (Abstract 2490), Circ. I-473 (1999).

Ho et al., *Dietary L-Arginine Reverses the Inhibitory Effect of Asymmetric Dimethylarginine on Angiogenesis in Hypercholesterolemia* (Abstract 407-2), JACC 33:1A (1999).

Huet et al., *Structural Homologies Between Two HLA B27-Restricted Peptides Suggest Residues Important for Interaction with HLA B27,* Intl. Immunol. 2(4):311-316 (1990).

Hutchison et al., *Effects of L-Arginine on Atherogenesis and Endothelial Dysfunction Due to Secondhand Smoke,* Hyperten. 34:44-50 (1999).

Jang et al., *Angiogenesis is Impaired by Hypercholesterolemia: Role of Asymmetric Dimethylarginine,* Circ. 102:1414-1419 (2000).

Jang et al., *L-Arginine Reverses the Anti-Angiogenic Effects of Asymmetric Dimethylarginine* (Abstract), J. Investi. Med. 4(2):86A (1999).

Jozkowicz et al., *Genetic Augmentation of Nitric Oxide Synthase Increases the Vascular Generation of VEGF,* Cardiovasc. Res. 51:773-783 (2001).

Kown et al., *Arginine Polymers Inhibit Graft Coronary Artery Disease Following Cardiac Transplantation* (Abstract 726), Transplant. 69(8):S300 (2000).

Kown et al., *L-Arginine Polymers Inhibit the Development of Vein Graft Neointimal Hyperplasia,* J. Thorac. Cardiovasc. Surg. 121(5):971-980 (2001).

Kown et al., *L-Arginine Polymer Mediated Inhibition of Graft Coronary Artery Disease After Cardiac Transplantation,* Transplant. 71(11):1542-1548 (2001).

Krejcy et al., *Distribution and Metabolism of $N^G$-Nitro-L-Arginine and $N^G$-Nitro-L-Arginine Methylester in Canine Blood* in vitro, Naunyn-Schmiedeberg's Arch. of Pharmacol. 347(3):342-345 (1993).

Krejcy et al., *Metabolism of L-$N^G$-Nitro Arginine Methyl Ester in Human and Canine Plasma* (Abstract 207), J. Mol. Cell. Cardiol. 24(Supp IV):S108 (1992).

Kyte et al., *A Simple Method for Displaying the Hydropathic Character of a Protein,* J. Mol. Biol. 157:105-132 (1982).

Latron et al., *Positioning of a Peptide in the Cleft of HLA-A2 by Complementing Amino Acid Changes,* PNAS 88:11325-11329 (1991).

Lieberman et al., *Estrogen Improves Endothelium-Dependent, Flow-Mediated Vasodilation in Postmenopausal Women,* Annals Intern. Med. 121(12):936-941 (1994).

Lieberman et al., *Flow-Induced Vasodilation of the Human Brachial Artery is Impaired in Patients <40 Years of Age with Coronary Artery Disease,* Am. J. Cardiol. 78:1210-1214 (1996).

Lim et al., *Acute Local Delivery of L-Arginine Reduces Long Term Intimal Thickening and Macrophage Infiltration* (Abstract 2346), Circ. 94(8):I403 (1996).

Lin et al., *Addition of a Poly Arginine Linker to Cyclosporin A Facilitates Transcutaneous Delivery and Topical Inhibition of Cutaneous Inflammation* (Abstract 155), J. Inv. Derm. 114(4):777 (2000).

Lissin et al., *Maintaining the Endothelium: Preventive Strategies for Vessel Integrity,* Prev. Cardio. 3:172-177 (2000).

Maxwell et al., *A Medical Food Designed to Enhance Nitric Oxide Activity Restores Endothelium-Dependent Function in Hypercholesterolemia* (Abstract 140), Nitric Oxide: Biology and Chemistry 4(3):251(2000).

Maxwell et al., *A Nutritional Product Designed to Enhance Nitric Oxide Activity Restores Endothelium-Dependent Function in Hypercholesterolemia,* J. Investi. Med. 47(2): 45A (1999).

Maxwell et al., *Cardiovascular Effects of L-Arginine,* Curr. Opin. Nephrol. Hyperten. 7:63-70 (1998).

Maxwell et al., *Endothelial Dysfunction in Hypercholesterolemia is Reversed by a Nutritional Product Designed to Enhance Nitric Oxide Activity,* Cardiovasc. Drugs Therapy 14:309-316 (2000).

Maxwell et al., *Improvement in Walking Distance and Quality of Life in Peripheral Arterial Disease by a Medical Food* (Abstract 86), Nitric Oxide: Biology and Chemistry, 4(3): 232 (2000).

Maxwell et al., *Improvement in Walking Distance and Quality of Life in Peripheral Arterial Disease by a Nutritional Product Designed to Enhance Nitric Oxide Activity* (Abstract), J. Investi. Med. 47(2):63A (1999).

Maxwell et al., *L-Arginine Attenuates the Impairment in Exercise Capacity Due to Hypercholesterolemia* (Abstract), JACC 29:265A (1997).

Maxwell et al., *L-Arginine Enhances Aerobic Exercise Capacity in Association with Augmented Nitric Oxide Production*, J. Appl. Physiol. 90:933-938 (2001).

Maxwell et al., *Limb Blood Flow During Exercise is Dependent on Nitric Oxide*, Circ. 98:369-374 (1998).

Maxwell et al., *Modulation of the Nitric Oxide Synthase Pathway in Atherosclerosis*, Exp. Physiol. 83:573-584 (1998).

Maxwell et al., *Nutritional Therapy for Peripheral Arterial Disease: A Double-Blind, Placebo-Controlled, Randomized Trial of HeartBar®*, Vasc. Med. 5:11-19 (2000).

Maxwell et al., *The Role of Nitric Oxide in Atherosclerosis*, Cor. Art. Dis. 10:277-286 (1999).

Meredith et al., *Role of Endothelium in Ischemic Coronary Syndromes*, Am. J. Cardiol. 72(8):27C-32C (1993).

Meredith et al., *Role of Impaired Endothelium-Dependent Vasodilation in Ischemic Manifestations of Coronary Artery Disease*, Circ. 87(5) Suppl:V56-V66 (1993).

Mitchell et al.; *Polyarginine Enters Cells More Efficiently than Other Polycationic Homopolymers*, J. Peptide Res. 56:318-325 (2000).

Miyazaki et al., *Endogenous Nitric Oxide Synthase Inhibitor: A Novel Marker of Atherosclerosis*, Circ. 99:1141-1146 (1999).

http://pysiology.cup.cam.ac.uk/Proceedings/Abstracts/523P/Birmingham/Files/S32.html, Musialek et al., *The Nitric Oxide Donor Sodium Nitroprusside Increases Heart Rate In The Absence Of Changes In Arterial Blood Pressure When Applied Topically To The Sino-Atrial Node In The Anaesthetized Pig*, J. Physiol. (2000), printed Jun. 12, 2001.

Niebauer et al., *Effects of Chronic Exercise in Patients with Chronic Heart Failure on Markers of Oxidative Stress* (Abstract 1019-10), JACC 33:172A (1999).

Niebauer et al., *Endothelium-Derived Nitric Oxide Attenuates Monocyte-Endothelial Interaction in Chronic Hypercholesterolemia* (Abstract 2014) Circ. 92(8)Suppl I:I-422 (1995).

Niebauer et al., *Endotoxin and Immune Activation in Chronic Heart Failure: A Prospective Cohort Study*, Lancet 353:1838-1842 (1999).

Niebauer et al., *Gene Transfer of Nitric Oxide Synthase: Effects on Endothelial Biology*, JACC 34(4):1201-1207 (1999).

Niebauer et al., *Local Delivery of L-Arginine After Balloon Angioplasty: Time Course of Intramural L-Arginine Activity, Nitric Oxide Production and Monocyte Binding* (Abstract 3082), Circ. 96:I-551 (1997).

Niebauer et al., *Local L-Arginine Delivery After Balloon Angioplasty Reduces Monocyte Binding and Induces Apoptosis*, Circ. 100:1830-1835 (1999).

Niebauer et al., *Oxidative Stress in Chronic Health Failure: Effects of Exercise* (Abstract P1652), Eur. Heart J. 20:305 (1999).

Niebauer et al., *Time Course of Intramural L-Arginine Activity, Nitric Oxide Production and Monocyte Binding Following Local L-Arginine Delivery After Balloon Angioplasty* (Abstract 251), Eur. Heart J. 19:14 (1998).

Ohno et al., *Shear Stress Elevates Endothelial cGMP: Role of a Potassium Channel and G Protein Coupling*, Circ. 88:193-197 (1993).

Raby et al., *Changing Vasomotor Responses of Coronary Arteries to Nifedipine*, Am. Heart J. 126(2):333-338 (1993).

Rothbard et al., *Conjugation of Arginine Oligomers to Cyclosporin A Facilitates Topical Delivery and Inhibition of Inflammation*, Nature Med. 6(11):1253-1257 (2000).

Rothbard et al., *Molecular Transporters Facilitate Topical Protein Transduction Into the Skin* (Abstract 957), J. Investi. Derm. 117(2):549 (2001).

Rothbard et al., *Reversal of HLA Restriction by a Point Mutation in an Antigenic Peptide*, Intl. Immunol. 1(4):487-495 (1989).

Safai et al., *L-Arginine/Nitric Oxide Pathway and Glomerular Injury in Preeclampsia* (Abstract A0504), J. Am. Soc. Nephrol. 9:98A (1998).

Schoolnik et al., *Gonococcal Pili: Primary Structure and Receptor Binding Domain*, J. Exp. Med. 159:1351-1370 (1984).

Schwarzacher et al., *L-$N^G$-Nitro-Arginine Methyl Ester in the Anesthetized Rabbit: Venous Vasomotion and Plasma Levels*, J. Vasc. Res. 29(3):290-292.

Schwarzacher et al., *Acute Local Delivery of L-Arginine Reduces Intimal Thickening and Macrophage Infiltration Following Balloon Injury in the Rabbit* (Abstract 2926), Eur. Heart J. 17:527 (1996).

Schwarzacher et al., *Assessment of Changes in Vasomotor Tone in vivo Using Intravascular Ultrasound*, J. Pharmacol. Toxicol. Meth. 28(3):143-147 (1992).

Schwarzacher et al., *Blockade of Endothelium-Derived Relaxing Factor Synthesis with $N^G$-Nitro-L-Arginine Methyl Ester Leads to Enhanced Venous Reactivity in vivo*, Eur. J. Pharmacol. 229(2/3):253-258 (1992).

Schwarzacher et al., *Local Delivery of L-Arginine Increases Vascular Nitric Oxide Production and Improves Endothelium-Dependent Vasomotion* (Abstract P492), Eur. Heart J. 17:82 (1996).

Schwarzacher et al., *Local Delivery of L-Arginine Increases Vascular Nitric Oxide Production and Improves Endothelium Dependent Vasomotion* (Abstract 779-6), JACC 27(2) Supp IA:288A (1996).

Schwarzacher et al., *Local Intramural Delivery of L-Arginine Enhances Nitric Oxide Generation and Inhibits Lesion Formation After Balloon Angioplasty*, Circ. 95(7):1863-1869 (1997).

Schwarzacher, *New Therapeutic Approaches for Correction of Endothelial Function After Balloon Dilatation* (Eng. Abstract), J Kardiologie 7(1):14-17 (2000).

Schwarzacher et al., *Altered Reactivity of the Inferior Vena Cava to Noradrenaline and Acetylcholine Following the Blockade of EDRF-Biosynthesis with $N^G$-Nitro-$_L$-Arginine Methyl Ester*, Clin. Exp. Pharmacol. Physiol. 23(6/7):490-492.

Selwyn et al., *Pathophysiology of Ischemia in Patients with Coronary Artery Disease*, Prog. Cardiovasc. Dis. XXXV(1):27-39 (1992).

http://www.pharmsci.org/scientificjournals/pharmsci/journal/99_7.html, Shameem et al., *A Short Term (Accelerated Release) Approach to Evaluate Peptide Release from PLGA Depot-Formulations*, Published Jul. 21, 1999, printed Feb. 19, 2002.

Sievers et al., *Low-Temperature Manufacturing of Fine Pharmaceutical Powders with Supercritical Fluid Aerosolization in a Bubble Dryer®*, Pure Appl. Chem. 73(8):1299-1303 (2001).

Singer et al., *Anti-Atherogenic Effect of the EDRF Precursor* (Abstract I20), Circ. 86(4) Suppl:78 (1992).

Singer et al., *Chronic Supplementation with L-Arginine, the Precursor of Endogenous Nitric Oxide, Causes Tolerance to Nitroglycerin*, Circ. 86(4) Suppl:1942 (1992).

Singer et al., *Dietary Supplements of L-Arginine Reduce Atherogenesis and Alter Vascular Reactivity in Hypercholesterolemic Animals* (Abstract) Clin. Res. 41(1): 78A (1993).

Singer et al., *Discordant Effects of Dietary L-Arginine on Vascular Structure and Reactivity in Hypercholesterolemic Rabbits*, J. Cardiovasc. Pharmacol. 25:710-716 (1995).

Stuehlinger et al., *Homocysteine Induced Accumulation of Asymmetric Dimethylarginine—Role of DDAH and Effect of Antioxidants* (Abstract 854), Circ. 102:II-177 (2000).

Suzuki et al., *Can Local Delivery of L-Arginine Reduce In-Stent Restenosis in Humans? An Ultrasound Volumetric Analysis* (Abstract 2459), Circ. 100(18) Suppl. I:I466-I467 (1999).

Tangphao et al., *Diurnal Variation of Plasma L-Arginine Concentrations and The Effect of Dietary L-Arginine Intake* (Abstract PII-25), Clin. Pharmacol. Therapeu. 63:178 (1998).

Tangphao et al., *L-Arginine and Nitric Oxide-Related Compounds in Plasma: Comparison of Normal and Arginine-Free Diets in a 24-h Crossover Study*, Vasc. Med. 4:27-32 (1999).

Theilmeier et al., *Adhesiveness of Mononuclear Cells in Hypercholesterolemic Humans is Normalized by Dietary L-Arginine*, Arterioscler. Thromb. Vasc. Biol. 17(12):3557-3564 (1997).

Theilmeier et al., *Adhesiveness of Mononuclear Cells is Increased in Hypercholesterolemic Humans, and Reduced by the NO Precursor* (Abstract 765-4), JACC 25:276A (1995).

Todd et al., *Regulation of Loblolly Pine (Pinus taeda L.) Arginase in Developing Seeding Tissue During Germination and Post-Germinative Growth*, Plant Mol. Biol. 45:555-565 (2001).

Tsao et al., *Anti-Platelet Effect of Dietary L-Arginine, the Nitric Oxide Precursor* (Abstract 732-6), JACC 21(2):Suppl A:125A (1993).

Tsao et al., *Dietary Arginine Alters Endothelial Adhesiveness via NO* (Abstract), Clin. Res. 42(2):175A (1994).

Tsao et al., *Dietary L-Arginine Reduces Platelet Reactivity in Hypercholesterolemic Rabbits* (Abstract), Clin. Res. 41(1):78A (1993).

Tsao et al., *Endothelial Alterations in Hypercholesterolemia: More Than Simply Vasodilator Dysfunction*, J. Cardiovasc. Pharmacol. 32(Suppl 3):S48-S53 (1998).

Tsao et al., *Enhanced Endothelial Adhesiveness in Hypercholesterolemia is Attenuated by L-Arginine*, Circ. 89:2176-2182 (1994).

Tsao et al., *Exposure to Shear Stress Alters Endothelial Adhesiveness: Role of Nitric Oxide*, Circ. 92(12):3513-3519 (1995).

Tsao et al., *Fluid Flow Inhibits Endothelial Adhesiveness: Nitric Oxide and Transcriptional Regulation of VCAM-1*, Circ. 94(7):1682-1689 (1996).

Tsao et al., *L-Arginine Attenuates Platelet Reactivity in Hypercholesterolemic Rabbits*, Arterioscler. Thromb. 14(10):1529-1533 (1994).

Tsao et al., *Nitric Oxide Regulates Monocyte Chemotactic Protein-1*, Circ. 96(3):934-940 (1997).

Uemura et al., *Rapid and Efficient Vascular Transport of Arginine Polymers Inhibits Myointimal Hyperplasia*, Circ. 102:2629-2635 (2000).

Uemura et al., *Short Polymers of Arginine Inhibit Myointimal Hyperplasia: Efficient Intracellular Translocation and Activation of Nitric Oxide Synthesis* (Abstract 411-2), JACC pp. 548A-549A (2000).

Uemura et al., *Short Polymers of Arginine Rapidly Translocate into Vascular Cells: Effect on Nitric Oxide Synthesis* (Abstract 64), Circ. 102(18) Suppl II:II-16 (2000).

Vita et al., *Patients with Evidence of Coronary Endothelial Dysfunction as Assessed by Acetylcholine Infusion Demonstrate Marked Increase in Sensitivity to Constrictor Effects of Catecholamines*, Circ. 85(4):1390-1397 (1992).

von der Leyen et al., *Gene Therapy Inhibiting Neointimal Vascular Lesion: in vivo Transfer of Endothelial Cell Nitric Oxide Synthase Gene*, PNAS 92:1137-1141 (1995).

von der Leyen et al., *Overexpression of Constitutive, Endothelial-Type Nitric Oxide Synthase As an in vivo Gene Transfer Approach to Prevent Neointima Formation After Vascular Injury*, Clin. Res. 42(2):180A (1994).

Walls et al., *Effects of Growth Factors and L-Arginine on Ischemic Skin Flaps in Rats*, Vet. Surg. 24:484-491 (1995).

Wang et al., *Arginine Prevents Atherogenesis in the Coronary Artery of the Hypercholesterolemic Rabbit* (Abstract 732-2), JACC 21(2) Suppl A:124A (1993).

Wang et al., *Arginine Restores Nitric Oxide Activity and Inhibits Monocyte Accumulation After Vascular Injury in Hypercholesterolemic Rabbits*, JACC 28(6):1573-1579 (1996).

Wang et al., *Dietary Arginine Prevents Atherogenesis in the Coronary Artery of the Hypercholesterolemic Rabbit*, JACC 23(2):452-458 (1994).

Wang et al., *Regression of Atherosclerosis: Role of Nitric Oxide and Apoptosis*, Circ. 99:1236-1241 (1999).

Wender et al., *An Efficient, Scalable Synthesis of the Molecular Transporter Octaarginine via a Segment Doubling Strategy*, Org. Letts. 3(21):3229-3232 (2001).

Wender et al., *The Design, Synthesis, and Evaluation of Molecules that Enable or Enhance Cellular Uptake: Peptoid Molecular Transporters*, PNAS 97(24):13003-13008 (2000).

Wolf et al., *Dietary L-Arginine Supplementation Normalizes Platelet Aggregation in Hypercholesterolemic Humans*, JACC 29(3):479-485 (1997).

Wong et al., *Antiatherogenic Effects of Dietary L-Arginine in the Systemic and Pulmonary Circulations in the Hypercholesterolemic Rabbit* (Abstract) Clin. Res. 41(2):212A (1993).

Yeung et al., *Interactions Between Mental Stress and Coronary Endothelial Dysfunction*, Homeostasis 34(5-6):244-251 (1993).

Yeung et al., *The Effect of Atherosclerosis on the Vasomotor Response of Coronary Arteries to Mental Stress*, N. Eng. J. Med. 325(22):1551-1556 (1991).

Zalpour et al., *Platelet Hyperaggregability in Hypercholesterolemic Humans: Reversal by Dietary L-Arginine* (Abstract 765-1), JACC p. 275A (1995).

Brochure, FreeZone CFC-Free Freeze Dry Systems, A Complete Guide to Laboratory Lyophilization Products, LABCONCO (2000).

http://www.temcoinstruments.com/product.html, Temco Instruments product information, *New Process for Rapid Micronization and Drying of Proteins, Pharmaceuticals and Other Particles*, printed Feb. 26, 2002.

http://www.uspharmacist.com/NewLook/CE/larginine/lesson.cfm, *The Role of L-Arginine in Cardiovascular Health*, U.S. Pharmacist Continuing Education, printed Sep. 12, 2002.

U.S. Appl. No. 10/177,156, filed Jun. 21, 2002, Michal et al.

U.S. Appl. No. 10/177,116, filed Jun. 21, 2002, Pacetti et al.

U.S. Appl. No. 10/177,114, filed Jun. 21, 2002, Simhambhatla et al.

U.S. Appl. No. 10/177,942, filed Jun. 21, 2002, Michal et al.

U.S. Appl. No. 10/176,506, filed Jun. 21, 2002, Claude et al.

U.S. Appl. No. 10/177,117, filed Jun. 21, 2002, Hossainy et al.

U.S. Appl. No. 10/320,899, filed Dec. 16, 2002, Shah et al.

Anonymous, Reducing the pH of a peptide oligomer to prepare for systemic delivery, Defensive Publication, Research Disclosure, p. 905 (Aug. 2003).

Anonymous, *Cardiologists Draw-Up The Dream Stent*, Clinica 710:15 (Jun. 17, 1996), http://www.dialogweb.com/cgi/document?reg=1061848202959, printed Aug. 25, 2003 (2 pages).

Anonymous, *Heparin-coated stents cut complications by 30%*, Clinica 732:17 (Nov. 18, 1996), http://www.dialogweb.com/cgi/document?reg=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?reg=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Katsarava et al., *Amino Acid-Based Bioanalogous Polymers. Synthesis and Study of Regular Poly(ester amide)s Based on Bis($\alpha$-amino acid)$\alpha$,$\omega$-Alkylene Diesters, and Aliphatic Dicarbolic Acids*, Journal of Polymer Science, Part A: Polymer Chemistry, 37(4), 391-407 (1999).

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjugate Chemistry 11(2):131-139 (Mar./Apr. 2000).

Peng et al., *Role of polymers in improving the results of stenting in coronary arteries*, Biomaterials 17:685-694 (1996).

Saotome, et al., *Novel Enzymatically Degradable Polymers Comprising $\alpha$-Amino Acid, 1,2-Ethanediol, and Adipic Acid*, Chemistry Letters, pp. 21-24, (1991).

Shigeno, *Prevention of Cerebrovascular Spasm By Bosentan, Novel Endothelin Receptor*, Chemical Abstract 125:212307 (1996).

van Buesekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

* cited by examiner

R= PG, H

Anhydride Coupling

1. $NH_2-(Arg)_x-COOH + PG \rightarrow PG-NH-(Arg)_x-COOH$

PG = protecting group

2. $PG-NH-(Arg)_x-COOH + ThOEt \rightarrow PG-NH-(Arg)_x-COOTh$

3.

4.

Imine coupling

R = L-arginine or L-arginine oligomer

FIG. 4

1.  PEI + glycidol → PEI-CH$_2$-CH(OH)-CH$_2$(OH) →[NaIO$_4$] PEI-CH$_2$-C(O)H + HC(O)H 2.  PEI-CH$_2$-CH(=O) + HCH(=O) + R → PEI-R  
                                                reductive amination 3.  PEI-R + heparin + carbodiimide → PEI-heparin-R PEI = polyethyleneimine Anhydride R = L-arginine or L-arginine oligomer Imine Ester

BIOCOMPATIBLE CARRIER CONTAINING L-ARGININE

BACKGROUND OF THE INVENTION

1. Field of the Invention

This invention relates to a biocompatible carrier containing L-arginine and L-arginine oligomers for introduction to a certain target cell population in a vascular region, such as smooth muscle cells or inflammatory cells, requiring modulation to ameliorate a diseased state, particularly for the treatment of stenosis or restenosis following a vascular trauma or disease. Moreover, the invention is directed to a composition containing L-arginine, or L-arginine oligomer thereof combined with a coating on an implantable device.

2. General Background and State of the Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location. Examples in patent literature disclosing stents which have been successfully applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results. One proposed method for medicating stents involves the use of a polymeric carrier coated onto the surface of a stent. A solution which includes a solvent, a polymer dissolved in the solvent, and a therapeutic substance dispersed in the blend is applied to the stent. The solvent is allowed to evaporate, leaving on the stent surface a coating of the polymer and the therapeutic substance impregnated in the polymer.

Local administration of therapeutic agents via stents has shown some favorable results in reducing restenosis. However, development of restenosis remains a persistent problem which has not been significantly alleviated by therapeutic substances which are currently used in the market. Accordingly, there is a great need for better and more effective therapeutic compositions, and methods of administering the compositions, for the effective treatment of restenosis.

Nitric oxide (NO) has many beneficial effects, including vasodilation and inhibiting smooth muscle cell hyperproliferation. However, the temporal, optical and hydrolytic instability of nitric oxide donor moieties has rendered them inefficient for use in reducing restenosis. For example, it is conventionally known that NO is a free radical, has a very short half life and is fast quenching. As a result, long term benefits of reducing restenosis would be difficult to achieve with the use of conventional NO donors.

L-arginine is an amino acid that can be loaded to a higher total effective dose of NO than a conventional NO donor. One of the advantages of using L-arginine as an NO donor is that the rate of NO release from L-arginine is controlled and sustained, which is an improvement over using conventional NO donors. In addition, several molecular components are required in the biosynthesis of nitric oxide from L-arginine including the enzymes iNOS and eNOS, with L-arginine often being the limiting reagent in this reaction scheme. When L-arginine is absorbed by a cell in the presence of eNOS, nitric oxide is produced. In view of the beneficial effects of NO in reducing restenosis, there is a need in the art for a sustained delivery of L-arginine or L-arginine oligomer released from a stent.

SUMMARY

The present invention has met the need for a more efficient and sustained method of delivering nitric oxide to a localized area by providing a method of sustained delivery of L-arginine or L-arginine oligomer from the hydrolysis of a polymer matrix from a prosthesis such as a stent.

Accordingly, the present invention is directed to a composition for inhibiting the narrowing of a blood vessel, comprising an oligomer of L-arginine, L-arginine, L-arginine analog, or L-arginine analog oligomer linked through a labile bond to a polymeric matrix, wherein the composition is used for coating an implantation device to inhibit the narrowing of the blood vessel. In this method, the composition may further comprise L-arginine, L-arginine analog, L-arginine oligomer, or L-arginine analog oligomer that is phase dispersed in the polymeric matrix. The oligomer may comprise more than 2 residues of L-arginine or L-arginine analog, or from 2 to 20 residues, from 2 to 15, from 2 to 9, from 2 to 7, or 7 residues. In the composition, the labile bond may be hydrolyzable by water. And the labile bond may be, but not limited to, an anhydride bond, ester bond, or imine bond.

The polymeric matrix may comprise poly(ethylene-co-vinyl alcohol), polyethylene glycol, acryloyl polyethylene glycol, poly(ethylene-co-glycidylmethacrylate), poly(ethylene-co-acrylic acid), poly(ethylene-co-maleic anhydride), hyaluronic acid, heparin, albumin, or glycosaminoglycan. The composition may also comprise a non-linking polymer. The non-linking polymer may be poly-n-butylmethacrylate, polyvinylidenefluoride, polyhexafluoropropylene, polycyclohexylmethacrylate, polyvinyledenefluoride-co-polyhexafluoropropylene, or hyaluronic acid.

The present invention is also directed to a coating for a prosthetic device, comprising a composition for inhibiting the narrowing of a blood vessel, comprising an oligomer of L-arginine, L-arginine, L-arginine analog, or L-arginine analog oligomer linked through a labile bond to a polymeric matrix. The prosthesis may be selected from a group of balloon-expandable stents, self-expandable stents, and grafts. The coating additionally may comprise a therapeutically active ingredient to be used in combination with the composition. The therapeutically active ingredient may be selected from a group of antineoplastic, anti-inflammatory, antiplatelet, anticoagulant, antifibrin, antithrombin, antimitotic, antiproliferative, antibiotic, antioxidant substances, and combinations thereof.

In another aspect, the invention is directed to a method of coating a surface of a prosthesis with a coating that comprises a composition for inhibiting the narrowing of a blood vessel, comprising an oligomer of L-arginine or L-arginine analog linked through a labile bond to a polymeric matrix, which method comprises spraying the coating on to a prosthesis or immersing the prosthesis in a solution of the coating.

In another embodiment, the invention is directed to a method of inhibiting restenosis of a blood vessel comprising depositing into a designated region of the blood vessel the L-arginine composition discussed above, wherein the composition is coated on to a prosthetic device.

The present invention is also directed to a stent coated with a coating comprising a composition for inhibiting the narrowing of a blood vessel, comprising an oligomer of L-arginine, L-arginine, L-arginine analog, or L-arginine analog oligomer linked through a labile bond to a polymeric matrix. And the stent further comprises a therapeutically active ingredient to be used in combination with the composition.

These and other embodiments of the invention will be more fully understood from the following referenced drawing attached hereto, description of the invention, and the claims appended hereto.

BRIEF DESCRIPTION OF THE DRAWINGS

FIG. 4 shows a reaction scheme for forming a polyethyleneimine-heparin-L-arginine coupling from polyethyleneimine starting material.

DETAILED DESCRIPTION

Figure 1:
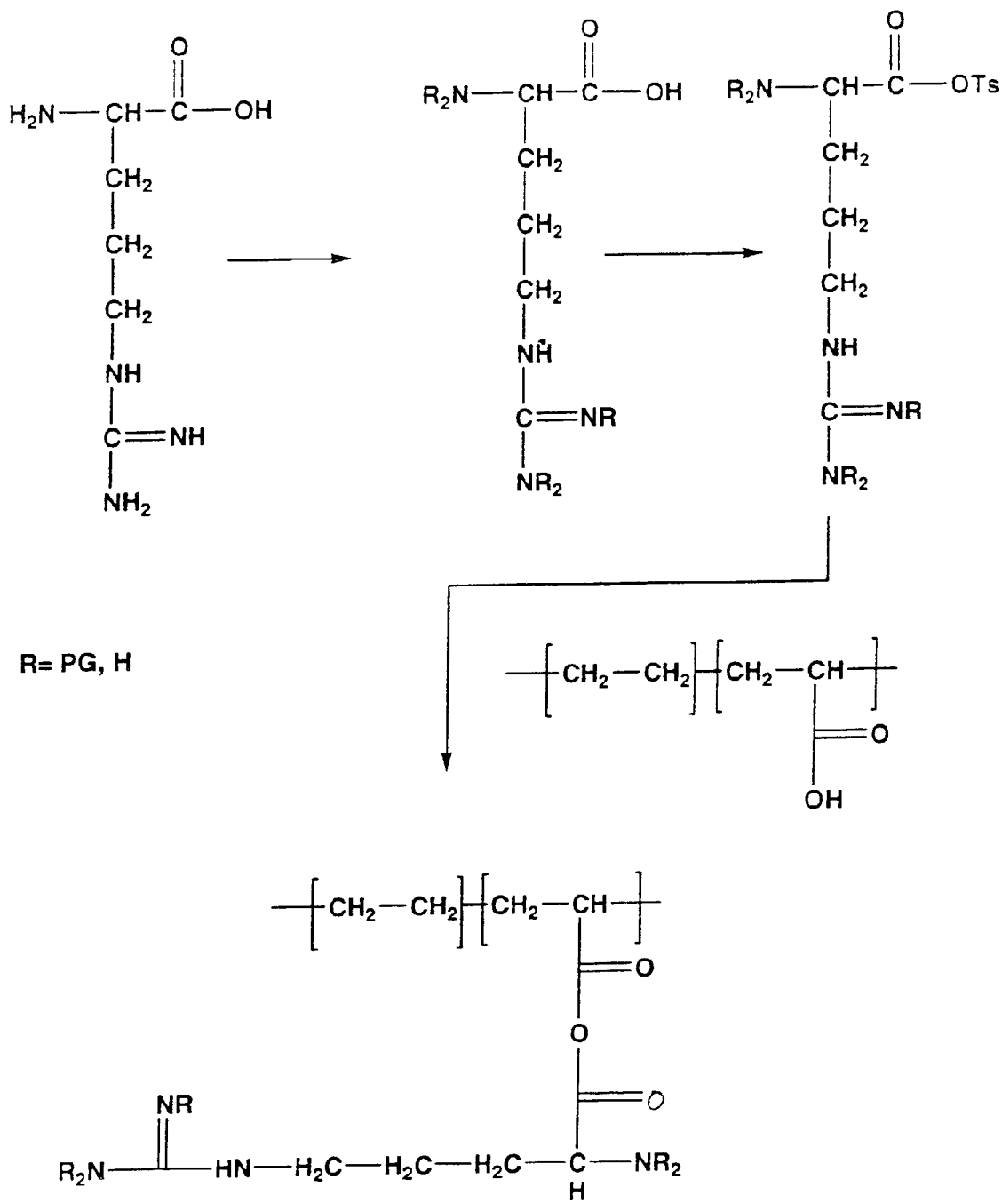
FIG. 1 shows a reaction scheme for forming an ester coupling of L-arginine to poly (ethylene-co-vinyl alcohol).

As used herein, "abnormal" or "inappropriate" proliferation means division, growth or migration of cells occurring more rapidly or to a significantly greater extent than which typically occurs in a normally functioning cell of the same type, i.e., hyperproliferation.

As used herein, "analogs" or "derivatives" refers to L-arginine or any variation of it that retains the biological activity of L-arginine, so long as it is capable of acting as a substrate of nitric oxide production.

As used herein, "inhibiting" cellular activity means reducing, delaying or eliminating smooth muscle cell hyperplasia, restenosis, vascular occlusions, platelet activation, or inflammatory response, particularly following biologically or mechanically mediated vascular injury or trauma or under conditions that would predispose a mammal to suffer such a vascular injury or trauma. As used herein, the term "reducing" means decreasing the intimal thickening that results from stimulation of smooth muscle cell proliferation. "Delaying" means retarding the progression of the hyperproliferative vascular disease or delaying the time until onset of visible intimal hyperplasia, as observed, for example, by histological or angiographic examination. "Elimination" of restenosis following vascular trauma or injury means completely "reducing" and/or completely "delaying" intimal hyperplasia in a patient to an extent which makes it no longer necessary to surgically intervene, i.e., to re-establish a suitable blood flow through the vessel by, for example, repeat angioplasty, atheroectomy, or coronary artery bypass surgery. The effects of reducing, delaying, or eliminating restenosis may be determined by methods known to one of ordinary skill in the art, including, but not limited to, angiography, ultrasonic evaluation, fluoroscopy imaging, fiber optic visualization, or biopsy and histology. Biologically mediated vascular injury includes, but is not limited to injury caused by or attributed to autoimmune disorders, alloimmune related disorders, infectious disorders including endotoxins and herpes viruses such as cytomegalovirus, metabolic disorders such as atherosclerosis, and vascular injury resulting from hypothermia and irradiation. Mechanical mediated vascular injury includes, but is not limited to vascular injury caused by catheterization procedures or vascular scraping procedures such as percutaneous transluminal coronary angioplasty, vascular surgery, stent placement, transplantation surgery, laser treatment, and other invasive procedures which disrupted the integrity of the vascular intima or endothelium. The active ingredient of the invention is not restricted in use for therapy following vascular injury or trauma; rather, the usefulness of the active ingredient will also be determined by the ingredient's ability to inhibit cellular activity of smooth muscle cells or inhibit the development of restenosis.

As used herein, "L-arginine" includes L-arginine that may be isolated from nature or chemically synthesized. Various forms of L-arginine may be also indicated where L-arginine may be in either a monomeric or an oligomeric form. By derivatives or analogs of "L-arginine," it is meant to refer to modifications of the compound that do not affect its ability to act as a substrate for nitric oxide production. L-arginine is used hereinafter without explicitly referring to those derivatives and analogs which are modifications. It is understood that by "L-arginine," those derivatives and analogs that act as a substrate for nitric oxide production may be included.

As used herein, "linking polymer" or "linking type polymer" refers to those polymers, copolymers, etc. that have the capability to bind to L-arginine or oligomers of L-arginine through a bond, e.g., labile bond. Such a labile bond may be generally cleaved by hydrolysis, thus releasing L-arginine or L-arginine oligomer.

As used herein, "migration" of smooth muscle cells means movement of these cells in vivo from the medial layers of a vessel into the intima, such as may also be studied in vitro by following the motion of a cell from one location to another, e.g., using time-lapse cinematography or a video recorder and manual counting of smooth muscle cell migration out of a defined area in the tissue culture over time.

As used herein, "non-linking polymer" or "non-linking type polymer" refers to those polymers that do not generally bind to L-arginine or oligomers of L-arginine.

As used herein, "oligomer" of L-arginine refers to at least two residues of L-arginine linked together. In particular, "R7" refers to a seven residue L-arginine oligomer. Following the same pattern, "R3" refers to a three residue L-arginine oligomer.

As used herein, "proliferation" of smooth muscle cells means increase in cell number.

As used herein, "smooth muscle cells" include those cells derived from the medial and adventitia layers of the vessel which proliferate in intimal hyperplastic vascular sites following vascular trauma or injury. Under light microscopic examination, characteristics of smooth muscle cells include a histological morphology of a spindle shape with an oblong nucleus located centrally in the cell with nucleoli present and myofibrils in the sarcoplasm. Under electron microscopic examination, smooth muscle cells have long slender mitochondria in the juxtanuclear sarcoplasm, a few tubular elements of granular endoplasmic reticulum, and numerous clusters of free ribosomes. A small Golgi complex may also be located near one pole of the nucleus.

L-arginine Linked Polymeric Matrix

L-arginine and oligomers thereof may be covalently linked by a hydrolyzable bond to various polymers so that sustained release of nitric oxide can be effectuated. In the practice of the invention, various polymers possessing the capability to form hydrolyzable bonds with L-arginine or derivatives thereof may be used. In this regard, L-arginine may be linked to large biological molecules such as albumin, hyaluronic acid and glycosaminoglycans, as well as other large molecules such as heparin. Moreover, the L-arginine and L-arginine oligomers may bind to natural or synthetic polymers.

Examples of such polymers may be ones that form esters, anhydrides, or imines. It is understood that any polymer may be used in linking the L-arginine or L-arginine derivative to the polymer so long as the bond that is formed is hydrolyzable. Specifically useful polymers may include poly (ethylene-co-vinyl alcohol), commercially known as EVAL, and poly(ethylene-co- glycidylmethacrylate) (EGMA). Both of these polymers exemplify polymers that may form ester bonds with L-arginine or oligomers thereof. Another useful polymer is poly(ethylene-co-acrylic acid) (EAA) and poly(ethylene-co-maleic anhydride) (EMA), which may form an anhydride linkage with L-arginine or an L-arginine oligomer. In the instance where anhydride bonds are formed, the resultant stable polymer may undergo hydrolysis, thus releasing L-arginine.

In yet another embodiment of the invention, polymers having no functional groups to form any linkage with L-arginine may be also included in the polymeric matrix. Such polymers may include, but not limited to, poly-n-butylmethacrylate (PBMA), polyvinylidenefluoride (KYNAR) (PVDF), polyhexafluoropropylene (HFP), polycyclohexylmethacrylate (PCMA), poly(vinyledenefluoride-co-hexafluoropropylene), hyaluronic acid, and combinations thereof.

Active Agent

Sufficient amounts of an active agent can also be included in the matrix. The active agent should inhibit the activity of vascular smooth muscle cells. More specifically, the active agent is aimed at inhibiting abnormal or inappropriate migration and proliferation of smooth muscle cells.

Examples of the active or therapeutic agents that may be used in the invention in addition to L-arginine include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.) Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.) Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin, dexamethasone and functional analogs or structural derivatives thereof.

The dosage or concentration of the active ingredient required to produce a favorable therapeutic effect should be less than the level at which the active ingredient produces toxic effects and greater than the level at which non-therapeutic results are obtained. The dosage or concentration of the active ingredient required to inhibit the desired cellular activity of the vascular region can depend upon factors such as the particular circumstances of the patient; the nature of the trauma; the nature of the therapy desired; the time over which the ingredient administered resides at the vascular site; and if other therapeutic agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Prosthesis

The use of the matrix is not limited to stents and the coating can also be used with a variety of other medical devices. Examples of implantable medical devices, that can be used in conjunction with the embodiments of this invention include stent-grafts, grafts (e.g., aortic grafts), artificial heart valves, cerebrospinal fluid shunts, pacemaker electrodes, axius coronary shunts and endocardial leads (e.g., FINELINE and ENDOTAK, available from Guidant Corporation). The underlying structure of the device can be of virtually any design. The device can be made of a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention. "MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

Coating

L-arginine may be present in the matrix as a phase dispersion, or it may be linked to a polymer described above through a hydrolyzable bond. L-arginine may be present as a monomer, or it may be present as an oligomer. Thus, either of the monomeric or oligomeric form of L-arginine may be phase dispersed or linked to a polymer through a labile bond. It is also understood that a combination of phase dispersed monomer and/or oligomer of L-arginine may be mixed with polymer bound monomer and/or oligomer of L-arginine. The oligomeric version of L-arginine has a particularly advantageous feature. Without being bound by theory, it is believed that the oligomeric form is readily absorbed by the tissue, hence this form is effective in delivering nitric oxide to vessel walls.

L-arginine oligomer may comprise 2 or more L-arginine residues. Usefully, the oligomeric form may comprise from 2 to 20 L-arginine residues. Or, the oligomeric form may comprise from 2 to 15 residues. Still yet, the oligomeric form may comprise from 2 to 9 residues. Also, the oligomeric form may comprise from 2 to 7 residues. In particular, the oligomer has 7 residues. However, it is understood that the number of residues in the oligomer may be modified and optimized depending on the degree of control of the release rate that is desired.

It is also understood that multiple layers of coating may be used, so long as at least one of the layers contains a form of L-arginine linked through a hydrolyzable bond to the linking polymer. For example, a layer may be added to the L-arginine bearing layer and may include an active ingredient mixed with a non-linking polymer or a linking polymer linked to L-arginine. Alternatively, the layer may not have any active ingredient at all, and instead may comprise various polymers, which in effect would be used either as a primer layer or a barrier layer. By way of example only, and without limiting the scope of the invention, in one embodiment of the invention, the first coating layer may contain an active ingredient and a linking type polymer linked with L-arginine or an oligomer thereof. The second coating layer may contain either the same linking type polymer used in the first coating layer, or it may contain a different linking polymer linked with the L-arginine or oligomer thereof, with or without the presence of the active ingredient.

Another exemplary configuration may be that the first coating layer may contain an active ingredient along with a linking type polymer bound through a hydrolytically degradable bond with L-arginine or an oligomer thereof. The second coating layer may contain a non-linking type polymer with either the presence or absence of an active ingredient. In still another example, the first coating layer may contain an active ingredient and a linking type polymer linked to L-arginine, or an oligomer thereof, and the second coating layer may contain a mixture of non-linking polymers and linking polymers linked to various forms of L-arginine.

Further, in another configuration, the first coating layer may contain an active ingredient together with a non-linking polymer. The second coating layer may contain either the same non-linking type polymer used in the first coating layer, or it may contain a different non-linking polymer, with or without the presence of the active ingredient. Phase dispersed L-arginine may be interspersed in either or both of the layers.

Another exemplary configuration may be that the first coating layer may contain an active ingredient along with a non-linking type polymer. The second coating layer may contain a linking type polymer bound through a hydrolytically degradable bond with L-arginine or an oligomer thereof in either the presence or absence of an active ingredient. In still another example, the first coating layer may contain an active ingredient and a non-linking type polymer, and the second coating layer may contain a mixture of non-linking polymers and linking polymers linked to L-arginine and/or oligomers thereof.

It is understood that while in the above exemplifications, where only two coating layers are discussed, it is contemplated that many layers of coating comprising variations in the amount of active ingredient, non-linking polymers, linking polymers, and L-arginine and oligomers thereof, may be used in the practice of the invention as is desired, according to the nitric oxide release profile that is desired.

In one embodiment, it is contemplated that various forms of L-arginine, and in particular, the R7 oligomeric form of L-arginine, are phase dispersed in a polymeric matrix so that they are released first from the polymeric matrix upon contact with vessel walls. Thereafter, the L-arginine forms that are linked to the linking type polymers are released in a controlled manner as a result of cleavage of the labile bonds.

Figure 5:
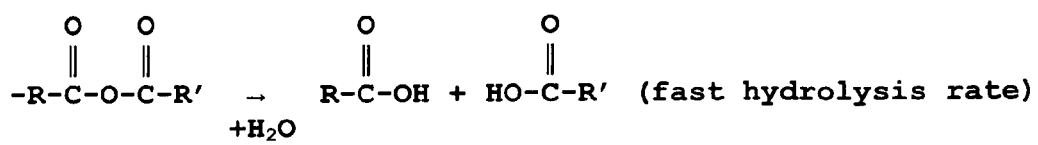
FIG. 5 shows compounds having various labile bonds, including anhydride, imine, and ester bonds, and their relative hydrolysis rates.
Figure 5:
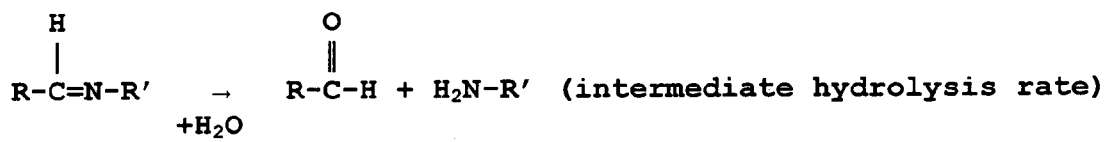
Figure 5:
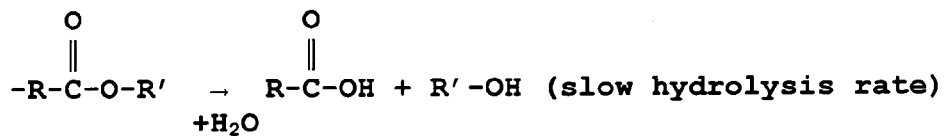

It is also contemplated that L-arginine or an oligomer thereof bound to linking polymers through various labile bonds may be released from the polymers in correlation to the type of labile bond that is being broken. Thus, a rate of release profile may be obtained according to the type of labile bonds that are present in the polymeric matrix. For instance, anhydride labile bonds are quickly broken upon contact with water. Imine bonds have an intermediate level of stability in the presence of water. Among the three exemplified labile bond types—anhydride, imine and ester bond—ester bonds are the most resistant to breakage in the presence of water. Thus, depending on the desires of the practitioner, a polymeric matrix may be formed comprising a mixture of these types of bonds to provide controlled release of L-arginine or oligomers thereof or any other active ingredient associated in the polymeric matrix. For example, if a quick release of the ligands from the polymeric matrix is desired, then the polymeric matrix should be composed of mostly anhydride bonds with the ligands. If a slow release of the ligands is desired, then the polymeric matrix should be comprised of mostly ester bonds. FIG. 5 shows the relative hydrolysis rates of various labile bonds.

An example of a polymeric matrix system would include a polymeric matrix comprising non-linking polymers and/or linking polymers. In particular, a copolymer such as acrylic-PEG-L-arginine may be blended with a matrix polymer such as EVAL, EVAL-PEG blend, or polyurethane. In addition, various forms of unbound L-arginine may be dispersed into the matrix so that a fast initial release rate of L-arginine is effected. This initial fast release rate may be followed by a more sustained and controlled delivery of L-arginine by hydrolytic cleavage of the labile bond according to the order of degradability of the bonds, resulting in the release of the ligands from the coupled copolymers.

Method of Use

In accordance with the above described method, the active ingredient and L-arginine or L-arginine oligomer can be applied to a prosthesis, e.g., a stent, retained on the stent during delivery and expansion of the stent, and released at a desired control rate and for a predetermined duration of time at the site of implantation. The release rate of the active ingredient can be controlled by modifying release parameters such as the amount of the comonomer content of the copolymer and the initial active ingredient content in the copolymer. The rate of release can also be adjusted by the addition of a second polymeric layer, with or without the active ingredient. A stent having the above described medicated coating is useful for a variety of medical procedures, including, by way of example, treatment of obstructions caused by tumors in bile ducts, an esophagus, trachea/bronchi and other biological passageways. A stent having the above described medicated coating is particularly useful for treating occluded regions of blood vessels caused by abnormal or inappropriate migration and proliferation of smooth muscle cells, thrombosis, and restenosis. Stents may be placed in a wide array of blood vessels, which include both arteries and veins. Representative examples of sites include the iliac, renal, and coronary arteries.

Briefly, an angiogram is first performed to determine the appropriate positioning for stent therapy. Angiography is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above described coating may then be expanded at the desired area of treatment. A post insertion angiogram may also be utilized to confirm appropriate positioning.

EXAMPLES

Example 1

Synthesis

To a 100 ml roundbottom flask is added a stirbar, condenser and nitrogen bubbler. Nitrogen is bubbled through the reaction flask. The EVAL is added to the flask and purged with nitrogen. Anhydrous DMAC is added to the flask using a cannula and nitrogen to push the nitrogen into the reaction flask. The flask is heated to 60° C. for 3 hours to dissolve the EVAL polymer. The polymer solution is then cooled to room temperature and the Nα-9-fluorenylmethoxycarbonyl (FMOC)-L-arginine is added and after about 2 minutes of stirring went into solution. The solution is then cooled to 0° C. and the 1 M dicyclohexylcarbodiimide (DCC) solution in methylenechloride (MeCl$_2$) is added dropwise. After the DCC is added, a crystal of dimethylaminopyridine (DMAP) is added to catalyze the esterification process. The solution is then stirred at 0° C. for 2 hours and allowed to warm to room temperature. The solution is then stirred under nitrogen for overnight. After stirring overnight, a significant concentration of white precipitate is formed in the reaction media. The reactants and amounts are shown in Table 1.

TABLE 1

Reactants for the Synthesis of Ester Linkage Between EVAL and L-arginine

| Reactant | Mass (grams) |
| --- | --- |
| Nα-FMOC-L-arginine | 1.6421 g |
| EVAL | 0.8452 g |
| N,N-dimethylacetamide | ~55 ml |
| DCC (1.0M in MeCl$_2$) | 5.2 ml |
| DMAP | 0.0201 g |

Example 2

Purification

The suspension is then added to a separatory funnel. To a flask is added 450 ml of water, 450 ml of methanol with 25 ml of 1N HCl. To the flask is then added the precipitate suspension in a dropwise manner. A white polymer is precipitated from the acidic methanol/water media, which is stirred for 15 minutes and then filtered under vacuum. The polymer is then re-dissolved in DMSO, filtered through a glass frit filter and re-precipitated into methanol/water forming a white fluffy precipitate. The sample is then dried under vacuum for overnight. The sample is extracted with methanol to remove residual DMAP and urea and dried under vacuum.

Example 3

Deprotection of FMOC from EVAL-(FMOC-L-arginine) Ester

To a roundbottom flask with a condenser and nitrogen source is added anhydrous N,N-dimethylacetamide, EVAL-(FMOC-L-arginine) ester and tetrabutylammonium fluoride. In the reaction of the deprotection, it is assumed that the yield for the esterification step is 100%. The calculations are shown in Table 2.

TABLE 2

Deprotection Reaction Reactants

| Reactants | Amount |
| --- | --- |
| EVAL-(FMOC-L-arginine)ester | 0.7696 g |
| DMAC | 50 ml |
| Tetrabutylammonium fluoride | 1.3688 g |

To a reaction flask is added the EVAL-(FMOC-L-arginine) ester and anhydrous DMAC under nitrogen. The sample is stirred and heated to 60° C. for 3 hours until the derivatized EVAL polymer went into solution. The solution is then cooled to room temperature. After the solution is cooled to room temperature, tetrabutylammonium fluoride is then added at room temperature, after which the solution turned a pink-red color. The solution is then stirred for 30 minutes.

Example 4

Purification of EVAL-Arginine Ester

The reaction solution is then added to 350 ml of deionized water while being vigorously stirred. The white polymer precipitate is then filtered and dried under vacuum. The polymer is re-dissolved into DMAC and then precipitated into methanol:ethanol (75:25). The suspension was then filtered and dried under vacuum. See FIG. 1 for the synthesis reaction.

Example 5

Anhydride Coupling of L-arginine or Oligomer Thereof

Figure 2:
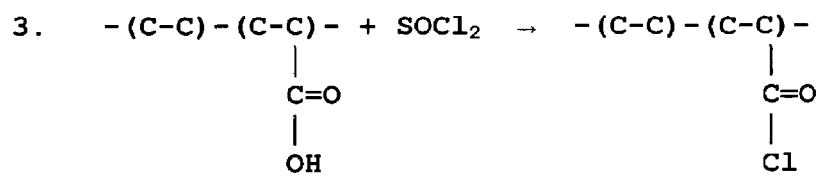
FIG. 2 shows a reaction scheme for forming an anhydride coupling of L-arginine to a poly (ethylene-co-acrylic acid).
Figure 2:
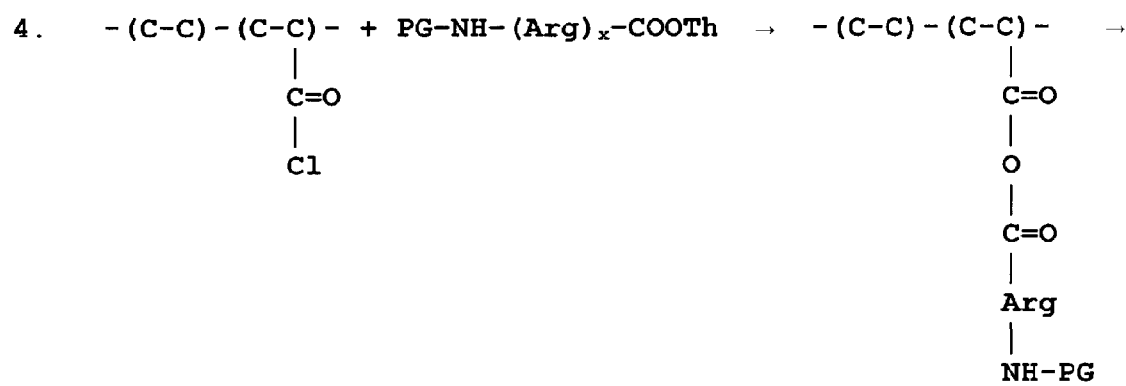
Figure 2:
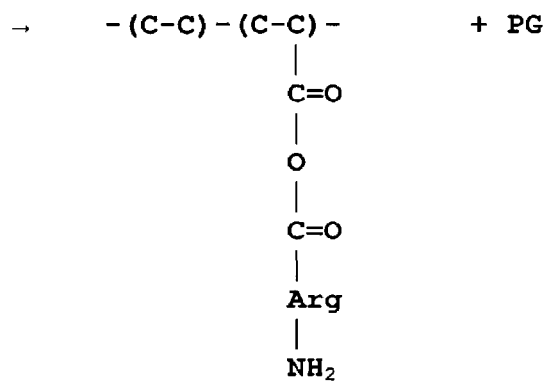

A method of obtaining an anhydride linkage between poly(butyl methacrylate-co-acrylic acid) and L-arginine or L-arginine oligomer is described. L-arginine is reacted with protecting groups to block the amino group of arginine. L-arginine is then reacted with thallium alkoxide to form a thallium salt to which polyethylene-co-acryloyl chloride is added. Then, the carboxylic acid moiety of poly (ethylene-co-acrylic acid) is converted to the acid chloride with thionyl chloride. After the completion of these reactions, the modified polymer is precipitated with anhydrous methanol, and then the L-arginine amine groups is are deprotected. After the deprotection of the amine, the polymer is extracted with anhydrous methanol to remove trace contaminants. See the reaction scheme in FIG. 2. The final product can contain about 50% by mass of the L-arginine component and about 20% by mass of acrylic acid functionality. The product is then dissolved in anhydrous ethanol, added to a dialysis tube (regenerated cellulose), and extracted with anhydrous ethanol. The polymer is then dried under vacuum.

Example 6

Ester Coupling of L-arginine or Oligomer Thereof

An acryloyl-PEG-OH group is reacted with the carboxy group of L-arginine to produce a polymer with a hydrolytically labile ester bond. This product is then further processed by copolymerizing with ethylmethacrylate, hydroxyethylmethacrylate, methylmethacrylate, or butylmethacrylate. The reaction product is then mixed with a matrix linking polymer and polymerized in situ on the stent to form an interpenetrating network, or alternatively, the acrylate group is polymerized separately in solution and mixed with a coating matrix and then applied to the stent.

Example 7

Ester Coupling of L-arginine or Oligomer Thereof

EVAL is linked to L-arginine or an L-arginine oligomer by forming an ester linkage. EVAL-L-arginine is then blended with a matrix polymer coating such as EVAL, EVAL-PEG blend, polyurethane and the like.

Example 8

A Labile Linkage Between L-arginine and EVAL

EVAL-L-arginine copolymer is blended with coating matrices comprising a PEG-superoxide dismutase donor or an EVAL-superoxide dismutase conjugate. EVAL-L-arginine copolymer may be also blended with coating matrices comprising an active ingredient.

Example 9

An Imine Linkage Between L-arginine and Polyethyleneimine

Figure 3:
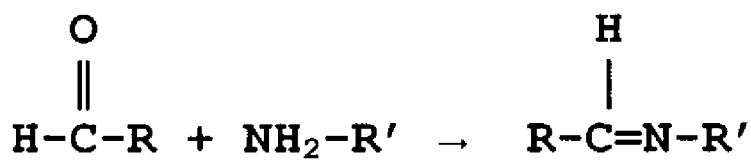
FIG. 3 shows a reaction scheme for forming an imine linkage between a suitable polymer and L-arginine.

Glycidol is used to modify polyethyleneimine (PEI), an amine-containing compound. A diamine spacer is first lengthened through the epoxide coupling of glycidol. So modified, the compound contains a spacer that terminates in vicinal diols. Periodate oxidation provides a formyl function at the end of the spacer. FIG. 3 shows a reaction scheme for forming the imine linkage. FIG. 4 shows the ligand coupling reaction using a periodate-oxidized glycidol spacer. Through further reductive amination of periodate activated PEI with L-arginine, and the addition of heparin and carbodiimide, PEI-heparin-L-arginine is formed.

Example 10

Compatible Single Phase Solution of R7 and EVAL

Step 1. Dissolve 0.13 grams EVAL in 3.6 grams DMAC.
Step 2. Dissolve 0.085 grams R7 in 1.6 grams methanol.
Step 3. While stirring the EVAL solution with a magnetic stir bar, add the R7/Methanol solution drop-wise. A stable, clear solution results. When sprayed onto a stent and dried, the resultant coating is clear and has high gloss, indicating a lack of gross phase separation in the dried film.

Example 11

Compatible Single Phase Solution of R7 and EVAL

Step 1. Dissolve 0.13 grams EVAL in 3.6 grams DMAC
Step 2. Dissolve 0.065 grams R7 in 1.5 grams methanol.
Step 3. While stirring the EVAL solution with a magnetic stir bar, add the R7/Methanol solution drop-wise. A stable, clear solution results. When sprayed onto a stent and dried, the resultant coating is clear and has high gloss, indicating a lack of gross phase separation in the dried film.

Example 12

Compatible Single Phase Solution of R7 and Poly n-butylmethacrylate (PBMA)

Step 1. Dissolve 0.2 grams PBMA in 3.3 grams DMAC.
Step 2. Dissolve 0.1 grams R7 in 1.4 grams methanol.
Step 3. While stirring the EVAL solution with a magnetic stir bar, add the R7/Methanol solution drop-wise. A stable, clear solution results. When sprayed onto a stent and dried, the resultant coating is clear and has high gloss, indicating a lack of gross phase separation in the dried film.

While particular embodiments of the present invention have been shown and described, it will be obvious to those skilled in the art that changes and modifications can be made without departing from this invention in its broader aspects and, therefore, the appended claims are to encompass within their scope all such changes and modifications as fall within the true spirit and scope of this invention.

What is claimed is:

1. A composition for inhibiting the narrowing of a blood vessel, comprising an oligomer of L-arginine, L-arginine, an L-arginine analog, or an L-arginine analog oligomer linked through a labile bond to a polymeric matrix, wherein the composition is used for coating an implantation device to inhibit the narrowing of the blood vessel.

2. The composition according to claim 1, wherein the L-arginine, the L-arginine analog, the L-arginine oligomer, or the L-arginine analog oligomer is phase dispersed in the polymeric matrix.

3. The composition according to claim 1, wherein the oligomer comprises from 2 to 20 residues of L-arginine or an L-arginine analog.

4. The composition according to claim 1, wherein the oligomer comprises from 2 to 9 residues of L-arginine or an L-arginine analog.

5. The composition according to claim 1, wherein the labile bond is hydrolyzable by water.

6. The composition according to claim 1, wherein the labile bond comprises an anhydride bond, ester bond, or imine bond.

7. The composition according to claim 1, wherein the polymeric matrix comprises poly(ethylene-co-vinyl alcohol), polyethylene glycol, acryloyl polyethylene glycol, poly(ethylene-co-glycidylmethacrylate), poly(ethylene-co-acrylic acid), poly(ethylene-co-maleic anhydride), hyaluronic acid, heparin, albumin, or a glycosaminoglycan.

8. The composition according to claim 1, wherein the composition comprises a non-linking polymer.

9. The composition according to claim 8, wherein the non-linking polymer is poly-n-butylmethacrylate, polyvinylidenefluoride, polyhexafluoropropylene, polycyclohexylmethacrylate, polyvinyledenefluoride-co-polyhexafluoropropylene, or hyaluronic acid.

10. A coating for a prosthetic device comprising a composition, the composition comprising an oligomer of L-arginine, L-arginine, an L-arginine analog, or an L-arginine analog oligomer linked through a labile bond to a polymeric matrix.

11. The coating according to claim 10, wherein the prosthesis is comprises a component selected from a group consisting of balloon-expandable stents, self-expandable stents, and grafts.

12. The coating of claim 10, additionally comprising an active agent carried by the polymeric matrix.

13. The coating of claim 12, wherein the active agent is effective for the treatment of restenosis.

14. A method of coating a prosthesis comprising coating the prosthesis with a composition comprising an oligomer of L-arginine, L-arginine, L-arginine analog, or L-arginine analog oligomer linked through a labile bond to a polymeric matrix.

15. The method of claim 14, wherein the prosthesis is comprises a component selected from a group consisting of balloon-expandable stents, self-expandable stents, and grafts.

16. The method of claim 14, wherein the coating additionally comprises an active agent effective for the treatment of restenosis.

17. A method of inhibiting restenosis of a blood vessel comprising depositing into a designated region of the blood vessel the composition according to claim 1, wherein the composition is coated on to a prosthetic device.

18. A stent coated with a coating comprising a composition for inhibiting the narrowing of a blood vessel, the composition comprising an oligomer of L-arginine, L-arginine, an L-arginine analog, or an L-arginine analog oligomer bonded linked through a labile bond to a polymeric matrix.

19. The stent according to claim 18, wherein the oligomer comprises from 2 to 20 residues of L-arginine or an L-arginine analog.

20. The stent according to claim 18, wherein the oligomer comprises from 2 to 9 residues of L-arginine or an L-arginine analog.

21. The stent according to claim 18, wherein the composition further comprises a labile bond that is hydrolyzable by water.

22. The stent according to claim 21, wherein the labile bond comprises an anhydride bond, an ester bond, or an imine bond.

23. The stent according to claim 18, wherein the polymeric matrix comprises poly(ethylene-co-vinyl alcohol), polyethylene glycol, acryloyl polyethylene glycol, poly(ethylene-co-glycidylmethacrylate), poly(ethylene-co-acrylic acid), poly(ethylene-co-maleic anhydride), hyaluronic acid, heparin, albumin, a glycosaminoglycan, poly-n-butylmethacrylate, polyvinylidenefluoride, polyhexafluoropropylene, polycyclohexylmethacrylate, polyvinyledenefluoride-co-polyhexafluoropropylene, or hyaluronic acid.

24. The coating according to claim 10, wherein the oligomer comprises from 2 to 20 residues of L-arginine or an L-arginine analog.

25. The coating according to claim 10, wherein the oligomer comprises from 2 to 9 residues of L-arginine or an L-arginine analog.

26. The coating according to claim 10, wherein the composition further comprises a labile bond that is hydrolyzable by water.

27. The coating according to claim 26, wherein the labile bond comprises an anhydride bond, an ester bond, or an imine bond.

28. The coating according to claim 10, wherein the polymeric matrix comprises poly(ethylene-co-vinyl alcohol), polyethylene glycol, acryloyl polyethylene glycol, poly(ethylene-co-glycidylmethacrylate), poly(ethylene-co-acrylic acid), poly(ethylene-co-maleic anhydride), hyaluronic acid, heparin, albumin, a glycosaminoglycan, poly-n-butylmethacrylate, polyvinylidenefluoride, polyhexafluoropropylene, polycyclohexylmethacrylate, polyvinyledenefluoride-co-polyhexafluoropropylene, or hyaluronic acid.

29. The method according to claim 14, wherein the oligomer comprises from 2 to 20 residues of L-arginine or an L-arginine analog.

30. The method according to claim 14, wherein the oligomer comprises from 2 to 9 residues of L-arginine or an L-arginine analog.

31. The method according to claim 14, wherein the composition further comprises a labile bond that is hydrolyzable by water.

32. The method according to claim 31, wherein the labile bond comprises an anhydride bond, an ester bond, or an imine bond.

33. The method according to claim 14, wherein the polymeric matrix comprises poly(ethylene-co-vinyl alcohol), polyethylene glycol, acryloyl polyethylene glycol, poly(ethylene-co-glycidylmethacrylate), poly(ethylene-co-acrylic acid), poly(ethylene-co-maleic anhydride), hyaluronic acid, heparin, albumin, a glycosaminoglycan, poly-n-butylmethacrylate, polyvinylidenefluoride, polyhexafluoropropylene, polycyclohexylmethacrylate, polyvinyledenefluoride-co-polyhexafluoropropylene, or hyaluronic acid.

* * * * *